(12) United States Patent
Yoon et al.

(10) Patent No.: US 11,938,123 B2
(45) Date of Patent: Mar. 26, 2024

(54) USE OF 2,3,5-SUBSTITUTED THIOPHENE COMPOUND TO PREVENT, AMELIORATE, OR TREAT BREAST CANCERS

(71) Applicant: Pharos iBio Co., Ltd., Anyang-si (KR)

(72) Inventors: Jeong Hyeok Yoon, Yongin-Si (KR); Ky Youb Nam, Goyang-Si (KR)

(73) Assignee: PHAROS IBIO CO., LTD. (KR)

( * ) Notice: Subject to any disclaimer, the term of this patent is extended or adjusted under 35 U.S.C. 154(b) by 723 days.

(21) Appl. No.: 17/059,046

(22) PCT Filed: May 29, 2019

(86) PCT No.: PCT/KR2019/006403
§ 371 (c)(1),
(2) Date: Nov. 25, 2020

(87) PCT Pub. No.: WO2019/231220
PCT Pub. Date: Dec. 5, 2019

(65) Prior Publication Data
US 2021/0205290 A1    Jul. 8, 2021

(30) Foreign Application Priority Data

May 30, 2018    (KR) .................. 10-2018-0061786

(51) Int. Cl.
| | | |
|---|---|---|
| *A61K 31/4535* | (2006.01) | |
| *A23L 33/10* | (2016.01) | |
| *A61K 45/06* | (2006.01) | |
| *A61P 35/00* | (2006.01) | |

(52) U.S. Cl.
CPC .......... *A61K 31/4535* (2013.01); *A23L 33/10* (2016.08); *A61K 45/06* (2013.01); *A61P 35/00* (2018.01)

(58) Field of Classification Search
CPC ...... A61K 31/4535; A61P 35/00; A23L 33/10
See application file for complete search history.

(56) References Cited

U.S. PATENT DOCUMENTS

| | | | |
|---|---|---|---|
| 2017/0196880 A1 | 7/2017 | Ocaña Fernández et al. | |
| 2019/0047993 A1 * | 2/2019 | Sim ...................... | C07D 333/10 |

FOREIGN PATENT DOCUMENTS

| | | |
|---|---|---|
| KR | 1020060127127 A | 12/2006 |
| KR | 1020130092561 A | 8/2013 |
| KR | 1020170096599 A | 8/2017 |
| WO | 2017132518 A1 | 8/2017 |
| WO | 2017142325 A1 | 8/2017 |
| WO | WO2017/142325 A1 * | 8/2017 |

OTHER PUBLICATIONS

Extended European Search Report corresponding to EP 19811107.2 dated May 11, 2022 (7 pages).
Bryant, Christopher, et al., "Chk1 Inhibition as a novel therapeutic strategy for treating triple-negative breast and ovarian cancers", BMC Cancer. 14:570 (2014).

* cited by examiner

*Primary Examiner* — Timothy R Rozof
(74) *Attorney, Agent, or Firm* — Myers Bigel, P.A.

(57) ABSTRACT

A composition for preventing, ameliorating or treating breast cancer, the composition containing a 2,3,5-substituted thiophene compound according to one embodiment of the present disclosure has an excellent activity of inhibiting the proliferation of breast cancers, particularly triple-negative breast cancer and Herceptin-resistant breast cancer, which have high mortality because there has yet been no effective therapeutic method therefor. Thus, the composition may be advantageously used for the prevention, amelioration or treatment of breast cancer.

5 Claims, 9 Drawing Sheets

FIG. 1 5
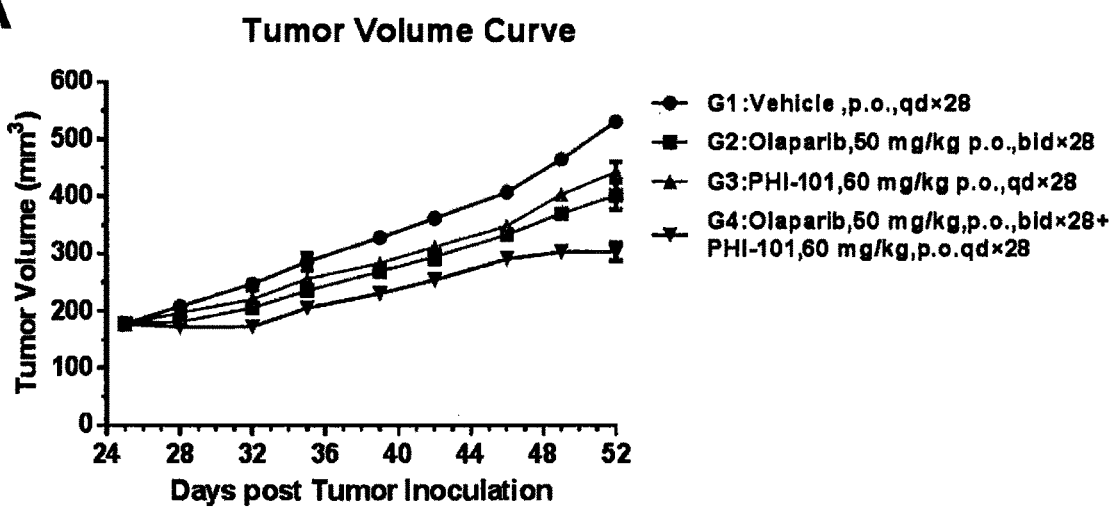
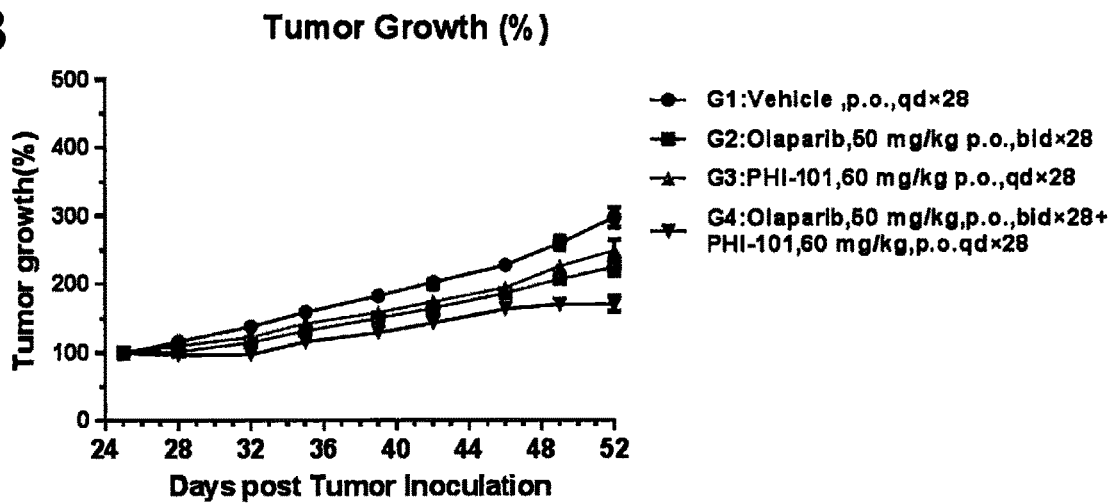

FIG. 16
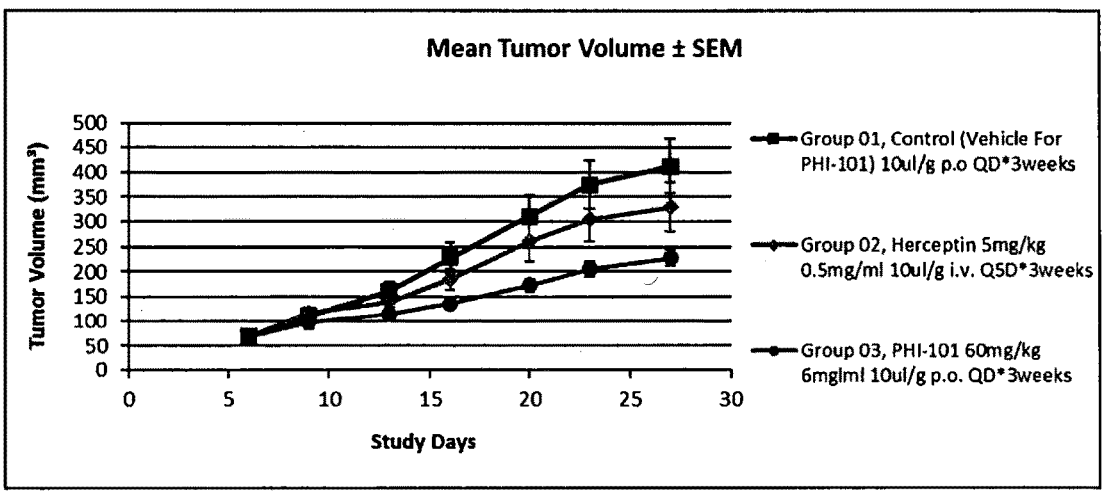
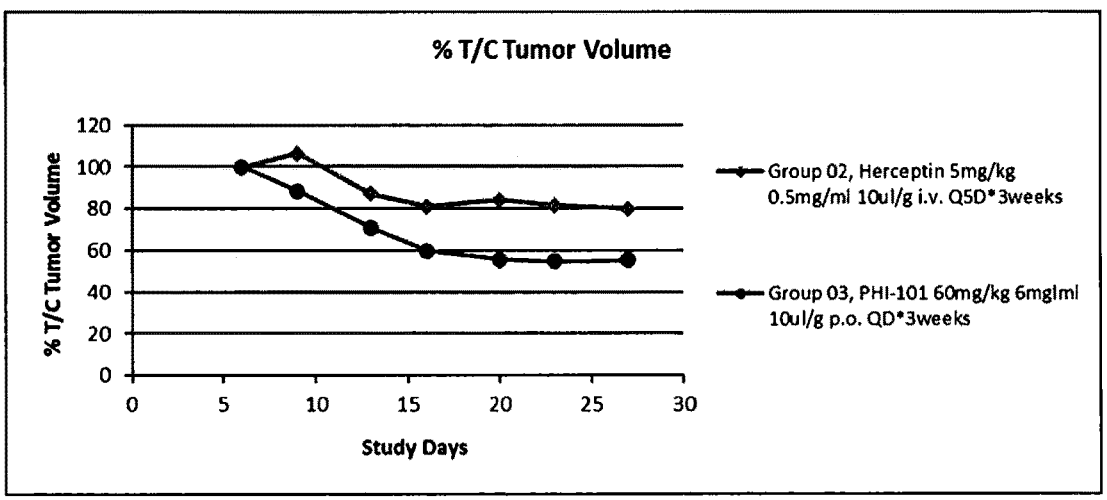
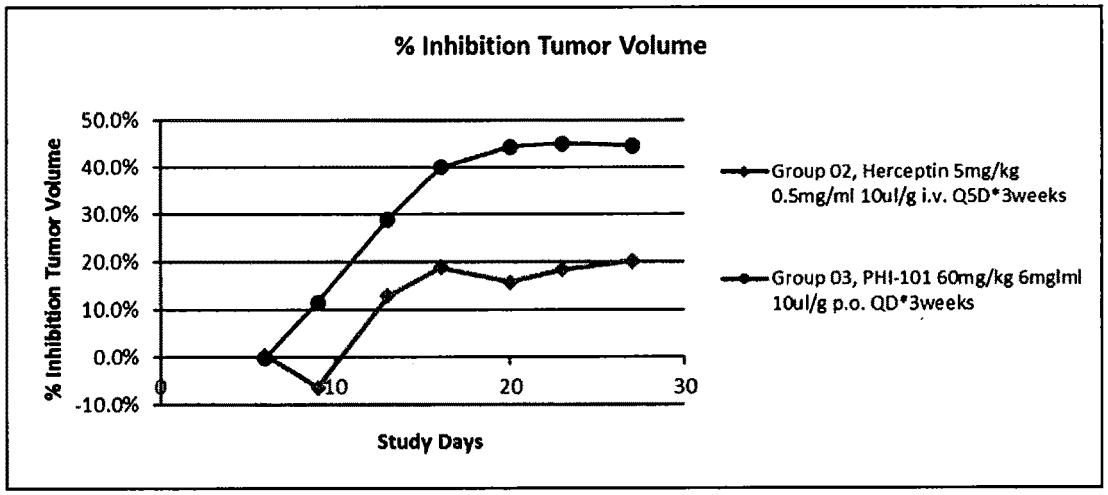

USE OF 2,3,5-SUBSTITUTED THIOPHENE COMPOUND TO PREVENT, AMELIORATE, OR TREAT BREAST CANCERS

CROSS REFERENCE TO RELATED APPLICATIONS

This application is a 35 U.S.C. § 371 national stage application of PCT International Application No. PCT/KR2019/006403, filed May 29, 2019, which claims priority from Korean Patent Application No. 10-2018-0061786, filed May 30, 2018, the contents of which are incorporated herein in their entireties by reference. The above-referenced PCT International Application was published in the Korean language as International Publication No. WO 2019/231220 A1 on Dec. 5, 2019.

TECHNICAL FIELD

The present disclosure relates to the use of a 2,3,5-substituted thiophene compound to prevent, ameliorate or treat breast cancer, and particularly, to the use of a 2,3,5-substituted thiophene compound to prevent, ameliorate or treat triple-negative breast cancer or Herceptin-resistant breast cancer.

The present disclosure was made with the support of the Korean government under grant number HI17C-2314-010017 ("Non-Clinical Study of New Candidate Compounds for Targeted Treatment of Acute Myelogenous Leukemia") awarded by the Ministry of Health and Welfare.

The present disclosure was made with the support of the Korean government under grant number S2531389 ("Global Development of Anticancer Drug of Second-Generation FLT3 Inhibitor PHI-101") awarded by the Small and Medium Business Administration.

BACKGROUND ART

With the development of modern medicine, many diseases have been treated and prevented, but cancer is still one of diseases difficult to treat. Currently, cancer is the first leading cause of death and continues to increase.

As a method for treating cancer, chemotherapy, surgical therapy and/or radiotherapy, etc. are used. Among them, chemotherapy is a method using an anticancer drug, and is most often used in the treatment of cancer. Today, about 60 kinds of various anticancer drugs are being used in clinical practice, and new anticancer drugs are continuously being developed as knowledge about cancer incidence and characteristics of cancer cells is sufficiently known. However, most of anticancer drugs that are currently used in clinical practice often cause adverse effects such as nausea, vomiting, ulcers of the oral cavity and small intestine, diarrhea, hair loss, and/or myelosuppression that results in the decreased production of blood active ingredients. For example, it is known that mitomycin-C has side effects such as renal failure, and adriamycin has adverse effects such as myelosuppression. In particular, cisplatin, which is the most useful drug among anticancer drugs developed so far, is widely used in the treatment of testicular cancer, ovarian cancer, lung cancer, head and neck cancer, bladder cancer, stomach cancer and cervical cancer, but has the big problem of showing adverse effects such as hematopoietic toxicities such as anemia, gastrointestinal toxicities such as vomiting and nausea, kidney toxicities such as kidney tubule damage, hearing loss, abnormalities in body electrolytes, shock, and peripheral nerve abnormalities.

New high-priced targeted anticancer drugs having excellent safety, which have recently been developed, exhibit efficacy in the treatment of many cancer patients, but exhibit efficacy only in a small group of patients by companion diagnosis. Therefore, there is an urgent need for precision medicine enabling personalized treatment in various cancer types.

Triple-negative breast cancer (TNBC) is defined as breast cancer without high expression of estrogen receptors (ER), progesterone receptors (PR) and HER2 receptors, and accounts for about 15% of the total breast cancer cases. The EGFR inhibitors cetuximab and erlotinib failed in clinical trials for triple-negative breast cancer, and the PARP1 inhibitor olaparib also did not show great efficacy in clinical trials in triple-negative breast cancer patients confirmed to have a BRCA mutation. As such, there has still been no effective targeted therapy for triple-negative breast cancer, and thus the mortality of triple-negative breast cancer is much higher than that of non-triple-negative breast cancer.

Herceptin (trastuzumab) is an anticancer agent targeting HER2 signaling, which is a means for stopping the growth of cancer cells having overexpression of HER2 protein. Herceptin has been shown to be effective in prolonging the survival of patients diagnosed with advanced breast cancer having HER2 overexpression, and is also known to reduce recurrence and death in patients with early stage breast cancer having HER2 protein overexpression or HER2 gene amplification. Accordingly, when patients are diagnosed with HER2-positive cancer, especially breast cancer, Herceptin is usually prescribed to the patients. However, it is known that many cases of cancer recurrence or even cancer metastasis occurred after a certain period of time in patients whose breast cancer was cured after the prescription of Herceptin, and the mechanism of acquisition of Herceptin resistance occurred as the cause thereof. In addition, since there is no effective therapeutic method for Herceptin-resistant breast cancer, the mortality thereof is much higher than that of common breast cancer.

Accordingly, the present inventors have conducted studies to discover an effective therapeutic agent for the treatment of breast cancer, thereby completing the present disclosure.

DISCLOSURE

Technical Problem

An object of the present disclosure is to provide the use of a compound represented by the following Formula 1 or a pharmaceutically acceptable salt thereof to prevent or treat breast cancer:

[Formula 1]

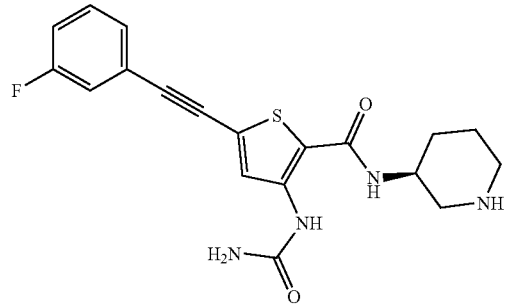

Technical Solution

One aspect of the present disclosure provides a pharmaceutical composition for preventing or treating breast cancer, the pharmaceutical composition containing a compound represented by the following Formula 1 or a pharmaceutically acceptable salt thereof:

[Formula 1]

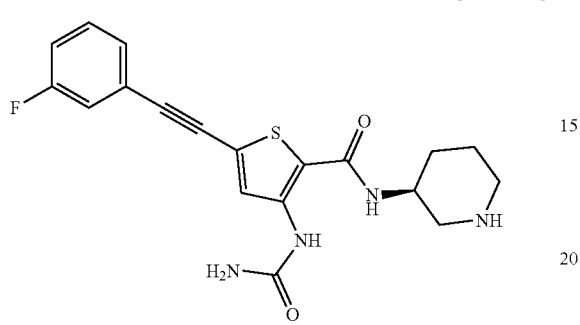

According to one embodiment of the present disclosure, the breast cancer may be triple-negative breast cancer.

According to one embodiment of the present disclosure, the composition may further contain cisplatin.

According to one embodiment of the present disclosure, the composition may further contain a poly(ADP-ribose) polymerase (PARP) inhibitor.

According to one embodiment of the present disclosure, the PARP inhibitor may be one or more anticancer drugs selected from the group consisting of olaparib, rucaparib, talazoparib and veliparib.

According to one embodiment of the present disclosure, the breast cancer may be Herceptin-resistant breast cancer.

According to one embodiment of the present disclosure, the pharmaceutically acceptable salt may be a hydrochloride salt.

Another aspect of the present disclosure provides a food composition for preventing or ameliorating breast cancer, the food composition containing a compound represented by the following Formula 1 or a pharmaceutically acceptable salt thereof:

[Formula 1]

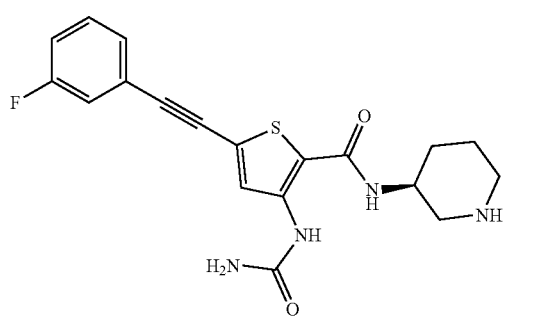

According to one embodiment of the present disclosure, the breast cancer may be triple-negative breast cancer or Herceptin-resistant breast cancer.

Still another aspect of the present disclosure provides a method for treating breast cancer, the method including a step of administering to a subject a pharmaceutical composition for preventing or treating breast cancer, the pharmaceutical composition containing a compound represented by the following Formula 1 or a pharmaceutically acceptable salt thereof:

[Formula 1]

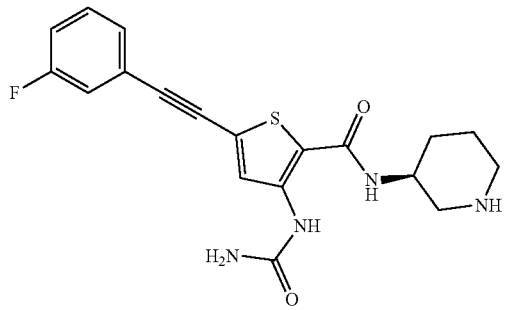

Advantageous Effects

The composition for preventing, ameliorating or treating breast cancer, the composition containing a 2,3,5-substituted thiophene compound according to one embodiment of the present disclosure has an excellent activity of inhibiting the proliferation of breast cancers, particularly triple-negative breast cancer and Herceptin-resistant breast cancer, which have high mortality because there has yet been no effective therapeutic method therefor. Thus, the composition may be advantageously used for the prevention, amelioration or treatment of breast cancer.

Figure 8:
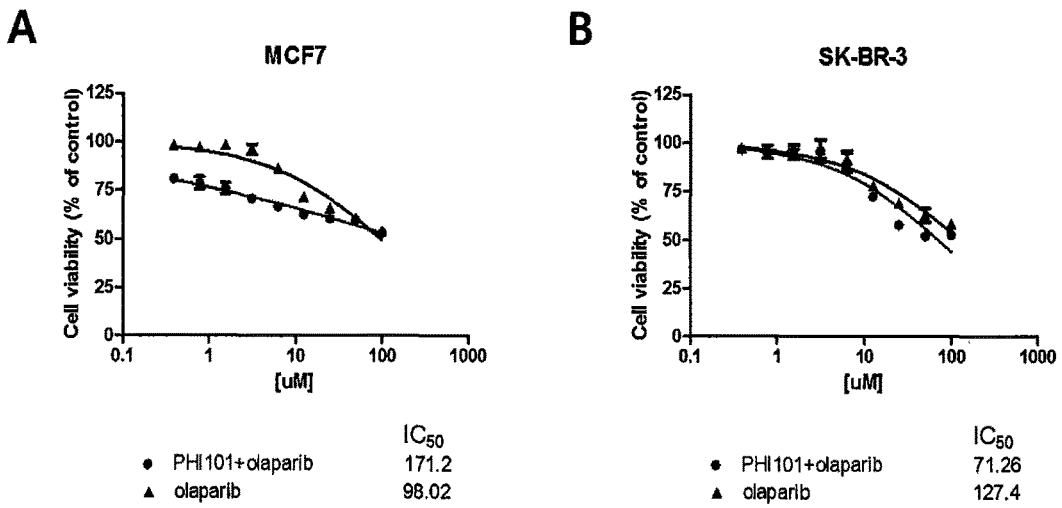

FIG. 8 depicts graphs showing the concentration-dependent effects of olaparib alone or a combination of PHI-101 and olaparib on the cell viabilities of MCF7 (A) and SK-BR-3 (B), which are non-triple-negative breast cancer cell lines.

Figure 9:
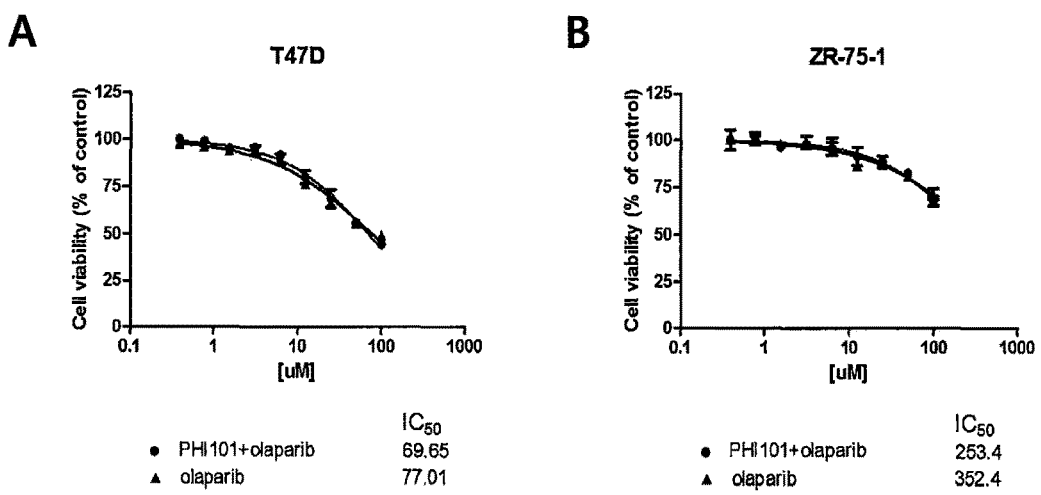

FIG. 9 depicts graphs showing the concentration-dependent effects of olaparib alone or a combination of PHI-101 and olaparib on the cell viabilities of T47D (A) and ZR-75-1 (B), which are non-triple-negative breast cancer cell lines.

Figure 10:
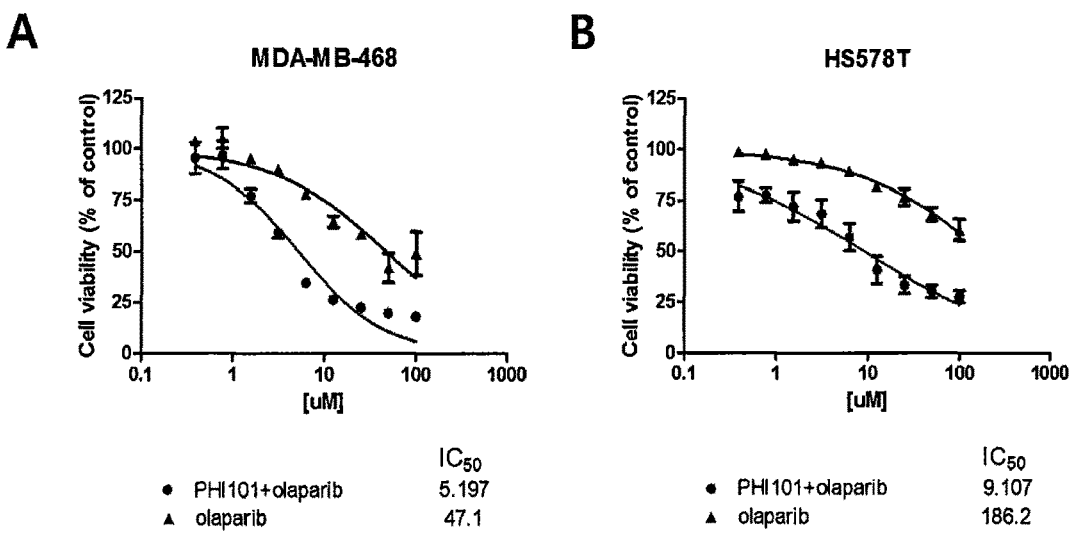

FIG. 10 depicts graphs showing the concentration-dependent effects of olaparib alone or a combination of PHI-101 and olaparib on the cell viabilities of MDA-MB-468 (A) and HS578T (B), which are triple-negative breast cancer cell lines.

Figure 11:
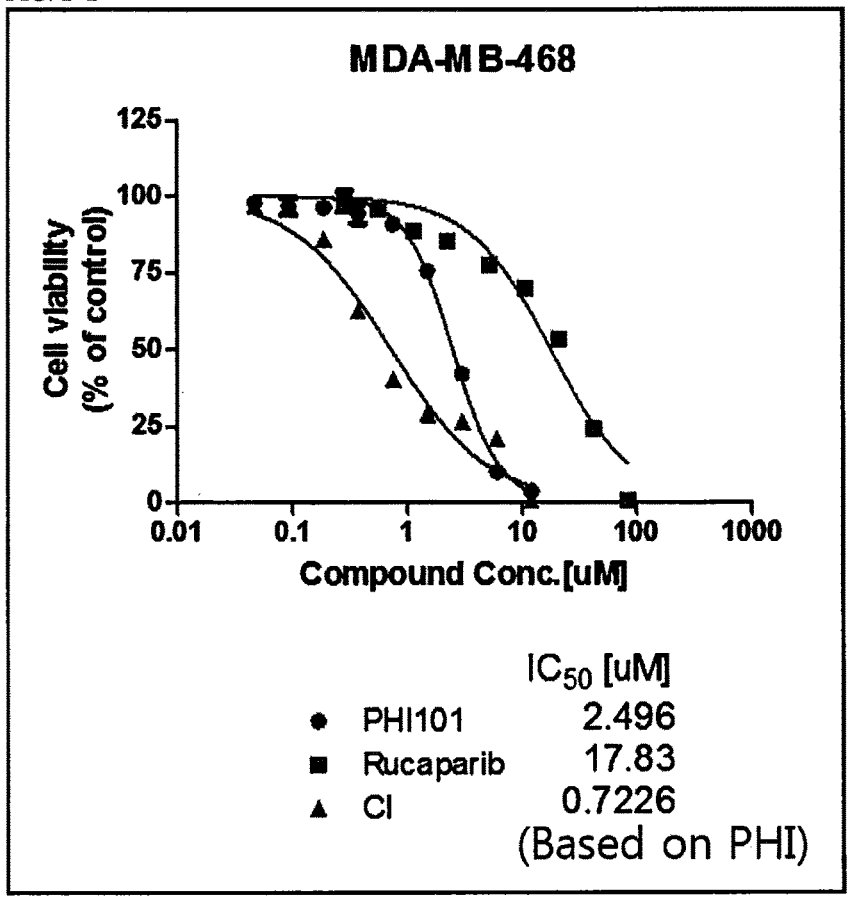

FIG. 11 depicts a graph showing the synergistic effect of a combination of rucaparib and PHI-101 (CI) on the cell viability of MDA-MB-468, which is a triple-negative breast cancer cell line, in the use of rucaparib alone, PHI-101 alone and the combination of rucaparib and PHI-101.

Figure 12:
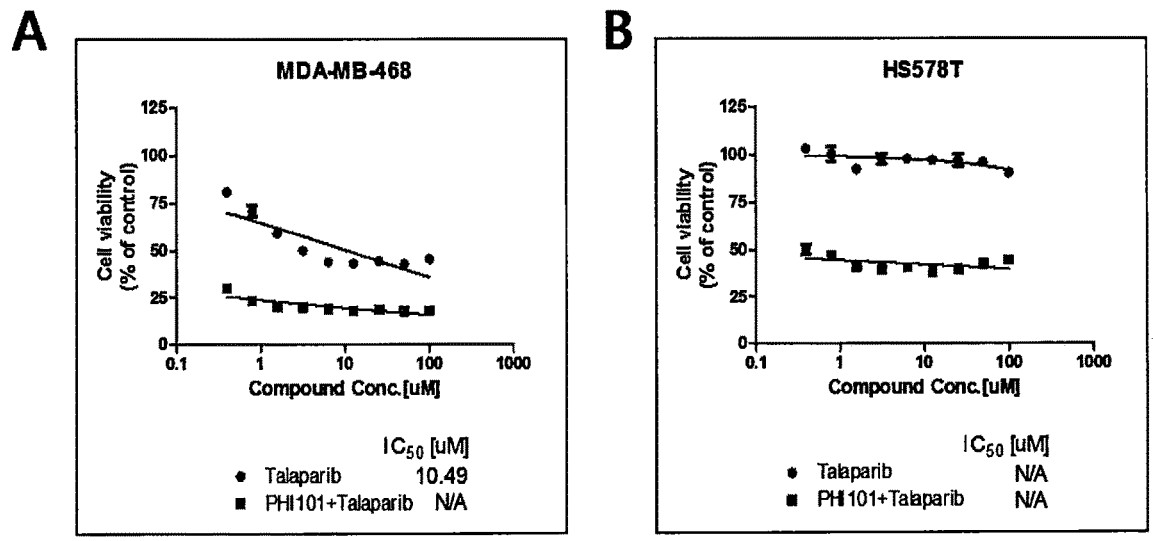

FIG. 12 depicts graphs showing the effects of talazoparib alone or a combination of PHI-101 and talazoparib on the cell viabilities of MDA-MB-468 (A) and HS578T (B), which are triple-negative breast cancer cell lines.

Figure 13:
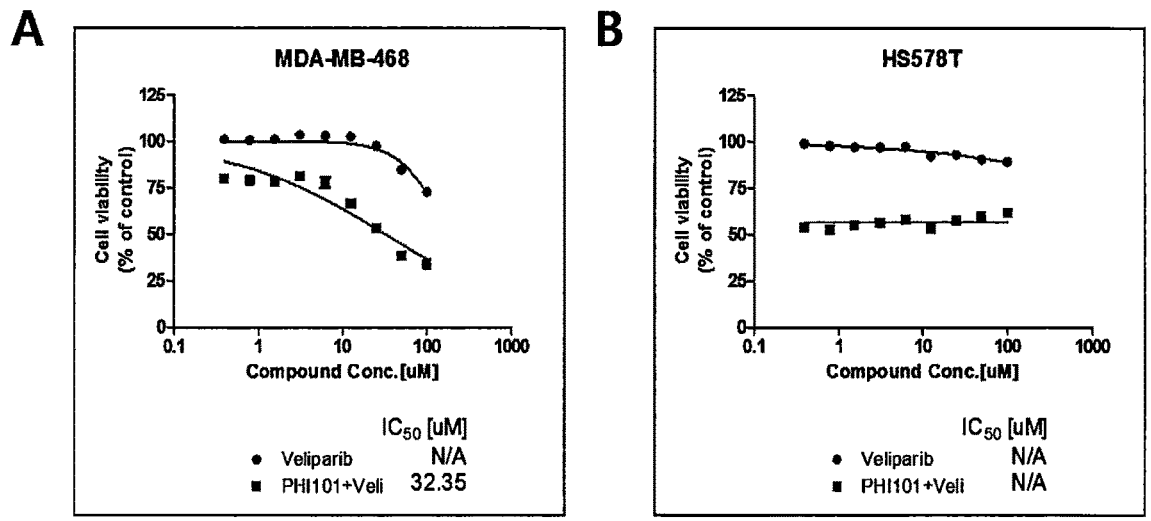

FIG. 13 depicts graphs showing the effects of veliparib alone or a combination of PHI-101 and veliparib on the cell viabilities of MDA-MB-468 (A) and HS578T (B), which are triple-negative breast cancer cell lines.

Figure 14:
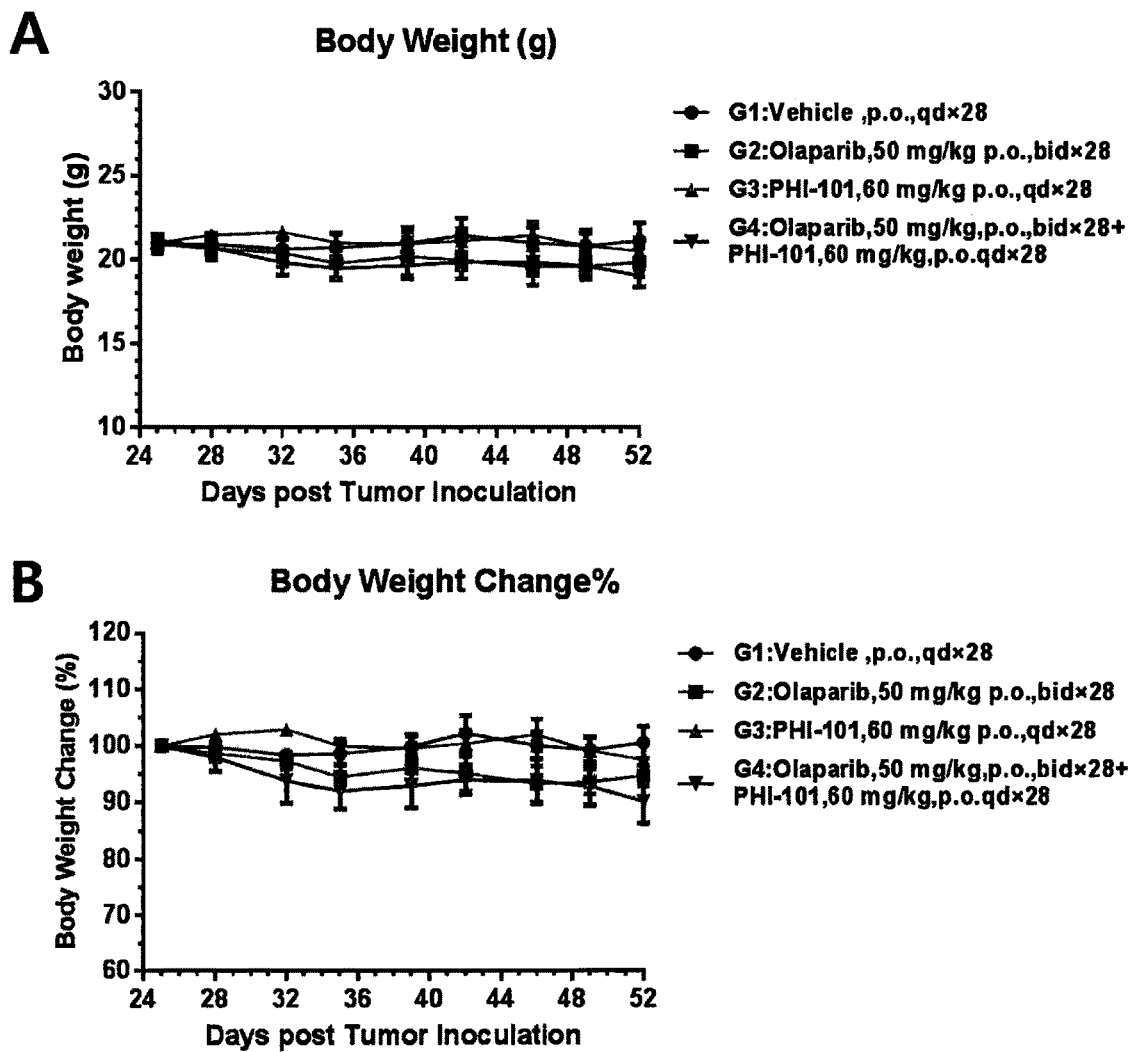

FIG. 14 depicts graphs showing the mouse body weight (A) and body weight change (B) resulting from the use of olaparib alone, PHI-101 or a combination of PHI-101 and olaparib in mice with tumors induced by MDA-MB-468 which is a triple-negative breast cancer cell line.

FIG. 15 depicts graphs showing the mouse tumor volume (A) and tumor growth (B) resulting from the use of olaparib alone, PHI-101 or a combination of PHI-101 and olaparib in mice with tumors induced by MDA-MB-468 which is a triple-negative breast cancer cell line.

FIG. 16 depicts graphs showing the mouse tumor volume (A), tumor T/C rate (B) and tumor inhibition rate (C) resulting from the use of Herceptin or PHI-101 in mice with tumors induced by JIMT-1 which is a Herceptin-resistant cell line.

BEST MODE

One aspect of the present disclosure provides a pharmaceutical composition for preventing or treating breast cancer, the pharmaceutical composition containing a compound represented by the following Formula 1 or a pharmaceutically acceptable salt thereof:

[Formula 1]

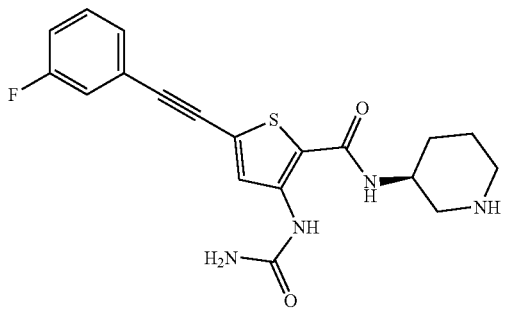

The compound represented by Formula 1, which is contained as an active ingredient in the pharmaceutical composition of the present disclosure, is (S)-5-((3-fluorophenyl)ethynyl)-N-(piperidin-3-yl)-3-ureido thiophene-2-carboxamide.

According to one embodiment of the present disclosure, the breast cancer may be triple-negative breast cancer.

The compound represented by Formula 1 has excellent ability to inhibit breast cancers, particularly triple-negative breast cancer and Herceptin-resistant breast cancer, which are specifically classified and have high mortality because there has yet been no effective therapeutic method therefor. Thus, this compound may be used alone or in combination with a conventional anticancer drug such as cisplatin or a PARP inhibitor, and when the compound is used in combination with the conventional anticancer drug, it may significantly enhance the breast cancer therapeutic effect of the conventional anticancer drug.

Although there is currently a problem in that there is no effective therapeutic method for triple negative breast cancer and Herceptin-resistant breast cancer, the compound represented by Formula 1 has excellent ability to inhibit the proliferation of triple-negative breast cancer and Herceptin-resistant breast cancer, and thus may be advantageously used for the prevention, amelioration or treatment of triple-negative breast cancer and Herceptin-resistant breast cancer.

The pharmaceutical composition according to one embodiment of the present disclosure may be administered together with one or more anticancer drugs.

According to one embodiment of the present disclosure, the composition may further contain cisplatin.

Cisplatin is an anticancer drug which is widely used for the treatment of testicular cancer, ovarian cancer, lung cancer, head and neck cancer, bladder cancer, stomach cancer and cervical cancer, but often causes adverse effects such as hematopoietic toxicities such as anemia, gastrointestinal toxicities such as vomiting and nausea, kidney toxicities such as kidney tubule damage, hearing loss, abnormalities in body electrolytes, shock, and peripheral nerve abnormalities.

It was confirmed that, when the compound represented by Formula 1 according to the present disclosure was used in combination with cisplatin, the breast cancer inhibitory effect thereof significantly increased compared to when the compound or cisplatin was used alone. In particular, it was confirmed that the combination of the compound and cisplatin showed a significantly lower $IC_{50}$ in triple-negative breast cancer than in non-triple-negative breast cancer. Thus, cisplatin may be administered at a lower concentration than when it is used alone, so that the occurrence of the aforementioned adverse effects by cisplatin may be minimized. Accordingly, the compound represented by Formula 1 according to the present disclosure may be used in combination with cisplatin to prevent or treat breast cancer, particularly triple-negative breast cancer.

According to one embodiment of the present disclosure, the composition may further contain a PARP inhibitor.

The term "PARP inhibitor" used in the present disclosure refers to a group that pharmaceutically inhibits poly(ADP-ribose) polymerase (PARP). Since various types of cancer are more sensitive to PARP than normal cells, the PARP inhibitor may inhibit the growth of cancer by inhibiting PARP. However, the PARP1 inhibitor olaparib is an anticancer drug that is used for breast cancer, but did not show a significant effect in clinical trials for triple-negative breast cancer patients confirmed to have a BRCA mutation.

In the present disclosure, it was confirmed that, when the compound represented by Formula 1 according to the present disclosure was used in combination with the PARP inhibitor olaparib, rucaparib, talazoparib or veliparib, the effect thereof on the inhibition of triple-negative breast cancer significantly increased compared to when the compound or the PARP inhibitor was used alone. Thus, the combination of the compound and the PARP inhibitor may exhibit an excellent anticancer effect compared to administration of the PARP inhibitor alone. Therefore, the compound represented by Formula 1 according to the present disclosure may advantageously be used in combination with the PARP inhibitor to prevent or treat triple-negative breast cancer showing resistance to the PARP inhibitor.

According to one embodiment of the present disclosure, the PARP inhibitor may be one or more anticancer drugs selected from the group consisting of olaparib, rucaparib, talazoparib and veliparib.

According to one embodiment of the present disclosure, the breast cancer may be Herceptin-resistant breast cancer.

Herceptin (trastuzumab) is an anticancer drug targeting HER2 signaling, which is a means for stopping the growth of cancer cells having overexpression of HER2 protein, but cancer cell resistance to Herceptin may occur due to the repeated use of Herceptin. Since there is no effective therapeutic drug for Herceptin-resistant breast cancer, it is inevitable to prescribe a combination formulation containing drugs such as expensive lapatinib in most cases. This prescription of combination formulation has a problem in that the prescription may cause overtreatment because it is not for patient-specific medical treatment, but for a number of different cases.

In the present disclosure, it was confirmed that the compound represented by Formula 1 according to the present disclosure had a significant inhibitory effect against Herceptin-resistant breast cancer. Therefore, the compound represented by Formula 1 according to the present disclosure may be advantageously used for the prevention or treatment of Herceptin-resistant breast cancer.

In addition, the pharmaceutical composition according to one embodiment of the present disclosure may be used alone or in combination with surgery, hormonal therapy, chemotherapy, radiotherapy and/or methods that use biological response modifiers, for the treatment of triple-negative breast cancer or Herceptin-resistant breast cancer.

The pharmaceutical composition of the present disclosure may contain a pharmaceutically acceptable carrier. Examples of the pharmaceutically acceptable carrier contained in the pharmaceutical composition of the present disclosure include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, which are commonly used in the manufacture of medicaments. The pharmaceutical composition of the present disclosure may further contain a lubricant, a wetting agent, a sweetening agent, a flavoring agent, an emulsifying agent, a suspending agent, a preservative, and the like, in addition to the above-described components. Suitable pharmaceutically acceptable carriers and formulations are described in detail in Remington's Pharmaceutical Sciences ($22^{nd}$ ed., 2013).

The pharmaceutical composition of the present disclosure may contain various bases and/or additives that are necessary and appropriate for formulation thereof. In addition, the pharmaceutical composition may be prepared to further contain known compounds such as a nonionic surfactant, a silicone polymer, an extender pigment, fragrance, a preservative, a disinfectant, an oxidation stabilizer, an organic solvent, an ionic or nonionic thickener, a softening agent, an antioxidant, a free radical destroying agent, an opacifying agent, a stabilizer, an emollient, silicone, α-hydroxyl acid, an antifoaming agent, a moisturizer, vitamins, an insect repellent, fragrance, a preservative, a surfactant, an anti-inflammatory agent, a substance P antagonist, a filler, a polymer, a propellant, a basifying or acidifying agent, or a colorant, within a range that does not impair the effects thereof.

A suitable dose of the pharmaceutical composition of the present disclosure may vary depending on factors such as formulation method, administration mode, the patient's age, body weight, sex, disease condition and diet, administration duration, administration route, excretion rate and response sensitivity. The dose of the pharmaceutical composition may be 0.001 to 1,000 mg/kg for an adult.

The pharmaceutical composition of the present disclosure may be administered orally or parenterally.

The pharmaceutical composition of the present disclosure may be administered orally in various forms, including tablets, pills, hard or soft capsules, solutions, suspensions, emulsions, syrups, granules, elixirs, troches, etc., and may further contain various excipients, for example, wetting agents, sweetening agents, flavoring agents, preservatives, and the like. Specifically, when the composition of the present disclosure is formulated in an oral dosage form, may further contain appropriate carriers, excipients and diluents, which are commonly used for formulation. As the carriers, excipients and diluents, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and/or mineral oil, may be used, but the examples thereof are not limited thereto. In addition, the composition may be prepared to contain fillers, extenders, binders, wetting agents, disintegrants, diluents such as surfactants, or excipients, which are generally used for formulation, and may further contain lubricants such as magnesium stearate or talc, in addition to the excipients.

The pharmaceutical composition of the present disclosure may be administered parenterally, for example, through a method such as subcutaneous injection, intravenous injection, intramuscular injection, or intrathoracic injection, but is not limited thereto.

Formulation into a dosage form for parenteral administration may be performed, for example, by mixing the pharmaceutical composition of the present disclosure with a stabilizer or buffer in water to prepare a solution or suspension, which may be prepared in a unit dosage form of an ampoule or vial. In addition, the composition may be sterilized, and may further contain adjuvants such as preservatives, stabilizers, hydrating agents or emulsification accelerators, salts and buffers for controlling osmotic pressure, as well as other therapeutically useful substances, and may be formulated by a conventional method.

According to one embodiment of the present disclosure, the pharmaceutically acceptable salt may be a hydrochloride salt.

Another aspect of the present disclosure provides a method for treating breast cancer, the method including a step of administering to a subject a pharmaceutical composition for preventing or treating breast cancer, the pharmaceutical composition containing the compound represented by Formula 1 as an active ingredient.

The pharmaceutical composition according to one embodiment of the present disclosure contains the compound represented by Formula 1 as an active ingredient, and exhibits an excellent anticancer effect against breast cancer, particularly triple-negative breast cancer or Herceptin-resistant breast cancer. Therefore, the method may further include a companion diagnosis step of selecting a group of patients on which the compound represented by Formula 1 shows an effect, before administering the pharmaceutical composition of the present disclosure. The companion diagnosis step may be performed by a triple-negative breast cancer diagnosis method or Herceptin-resistant breast cancer diagnosis method known in the art.

As used herein, the term "companion diagnosis" refers to diagnosis for predicting a patient's response to a specific chemotherapy treatment.

Still another aspect of the present disclosure provides a food composition for preventing or ameliorating breast cancer containing a compound represented by the following Formula 1 or a pharmaceutically acceptable salt thereof:

[Formula 1]

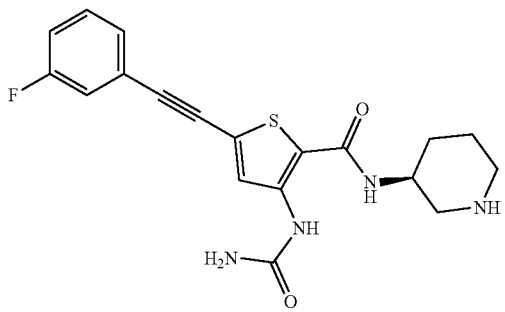

The food composition of the present disclosure may be prepared by adding raw materials and components that are commonly added in the art. The food composition may further contain various flavoring agents or natural carbohydrates, like conventional food compositions, in addition to containing the compound represented by Formula 1 as an active ingredient.

According to one embodiment of the present disclosure, the natural carbohydrates may be conventional sugars such as monosaccharides (e.g., glucose, fructose, etc.), disaccharides (e.g., maltose, sucrose, etc.), and polysaccharides (e.g., dextrin, cyclodextrin, etc.), and sugar alcohols such as xylitol, sorbitol and erythritol. The flavoring agents may include natural flavoring agents [thaumatin, stevia extract (e.g., rebaudioside A, glycyrrhizin, etc.)] and/or synthetic flavoring agents (saccharin, aspartame, etc.).

The food composition of the present disclosure may further contain one or more food-acceptable or pharmaceutically acceptable carriers for formulation, in addition to the above-described active ingredient. The dosage form of the food composition may be a tablet, capsule, powder, granule, liquid, pill, solution, syrup, juice, suspension, emulsion or drop formulation. For example, for formulation in the form of tablet or capsule, the active ingredient may be combined with an oral, non-toxic pharmaceutically acceptable inert carrier such as ethanol, glycerol and water.

The food composition of the present disclosure may contain a vitamin mixture composed of vitamin A acetate, vitamin E, vitamin B1, vitamin B2, vitamin B6, vitamin B12, vitamin C, biotin, nicotinic acid amide, folic acid, and calcium pantothenate, and one or more minerals such as ferrous sulfate, zinc oxide, magnesium carbonate, potassium phosphate monobasic, potassium phosphate dibasic, potassium citrate, calcium carbonate, and magnesium chloride, which may commonly added in the art.

If necessary, a suitable binder, lubricant, disintegrant and coloring agent may also be contained as a mixture. Suitable binders may include natural sugars such as starch, gelatin, glucose or beta-lactose, natural and synthetic gums such as corn sweeteners, gum acacia, tragacanth or sodium oleate, sodium stearate, magnesium stearate, sodium benzoate, sodium acetate, sodium chloride, and the like. Disintegrants may include starch, methyl cellulose, agar, bentonite, xanthan gum, and the like.

These components may be used independently or in combination, and the content of these additives may be selected within a range of 0 to about 20 parts by weight per 100 parts by weight of the food composition of the present disclosure, but is not limited thereto.

Meanwhile, it is possible to prepare a variety of foods by applying various formulation preparation methods, known to those skilled in the art, to the food composition of the present disclosure. For example, the food composition of the present disclosure may be prepared as common health functional food formulations such as beverages, pills and powders, but is not limited thereto.

According to one embodiment of the present disclosure, the breast cancer may be triple-negative breast cancer or Herceptin-resistant breast cancer.

The food composition of the present disclosure has particularly excellent ability to inhibit the proliferation of triple-negative breast cancer and Herceptin-resistant breast cancer cell lines, and thus may be advantageously used for the prevention or amelioration of triple-negative breast cancer and Herceptin-resistant breast cancer.

MODE FOR INVENTION

Hereafter, the present disclosure will be described in more detail with reference to one or more examples. However, these examples are to describe the present disclosure by way of example, and the scope of the present disclosure is not limited to these examples.

Example 1. Evaluation of Inhibitory Activity Against Breast Cancer Cell Lines

Each of the breast cancer cell lines shown in Table 1 below was cultured with DMEM (Dulbecco's Modified Eagle Medium) or RPMI1640 in a 100-mm culture dish (SPL) under 5% $CO_2$ at 37° C., and then diluted to a density of 3,000 cells/90 μl using PBS (phosphate-buffered saline) (Biosesang).

TABLE 1

| Cell line | Source | Cat # | Remarks |
|---|---|---|---|
| BT474 | ATCC | HTB-20 | Non-triple-negative breast cancer |
| JIMT1 | DSMZ | ACC589 | |
| MCF7 | ATCC | HTB-22 | |
| SK-BR-3 | ATCC | HTB-30 | |
| T47D | ATCC | HTB-133 | |
| ZR-75-1 | ATCC | CRL-1500 | |
| MDA-MB-231 | ATCC | HTB-26 | Triple-negative breast cancer |
| MDA-MB-435 | ATCC | HTB-129 | |

TABLE 1-continued

| Cell line | Source | Cat # | Remarks |
|---|---|---|---|
| MDA-MB-468 | ATCC | HTB-132 | |
| BT549 | ATCC | HTB-122 | |
| HCC1937 | ATCC | CRL-2336 | |
| HS578T | ATCC | HTB-126 | |

Next, 90 μl of each of the diluted breast cancer cell lines was treated with 10 μl of a 1:2 serial dilution of a hydrochloride salt of the compound represented by Formula 1 (hereinafter referred to as "PHI-101") to a final concentration of up to 100 μM, and then cultured under 5% $CO_2$ at 37° C. for 72 hours. After culture, the cells were counted using a Celltiter-Glo assay kit (Promega), and cell viability was measured by expressing the cell count as a percentage relative to that of a control group not treated with PHI-101.

[Formula 1]

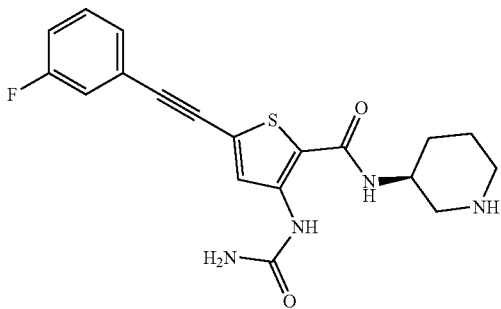

Figure 1:
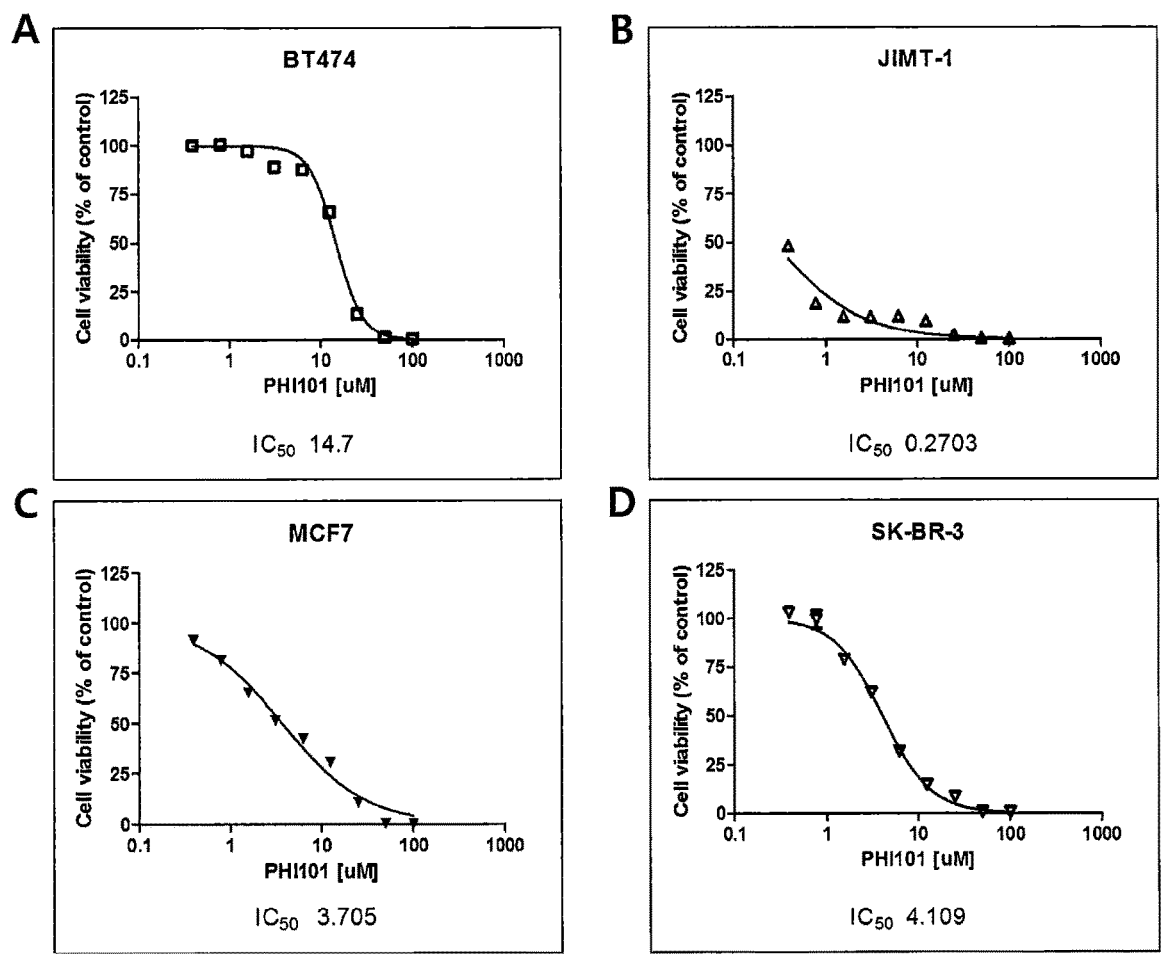
FIG. 1 depicts graphs showing the concentration-dependent effects of a compound (PHI-101) represented by Formula 1 on the cell viabilities of BT474 (A), JIMT1 (B), MCF7 (C) and SK-BR-3 (D), which are non-tripe-negative breast cancer cell lines.
Figure 2:
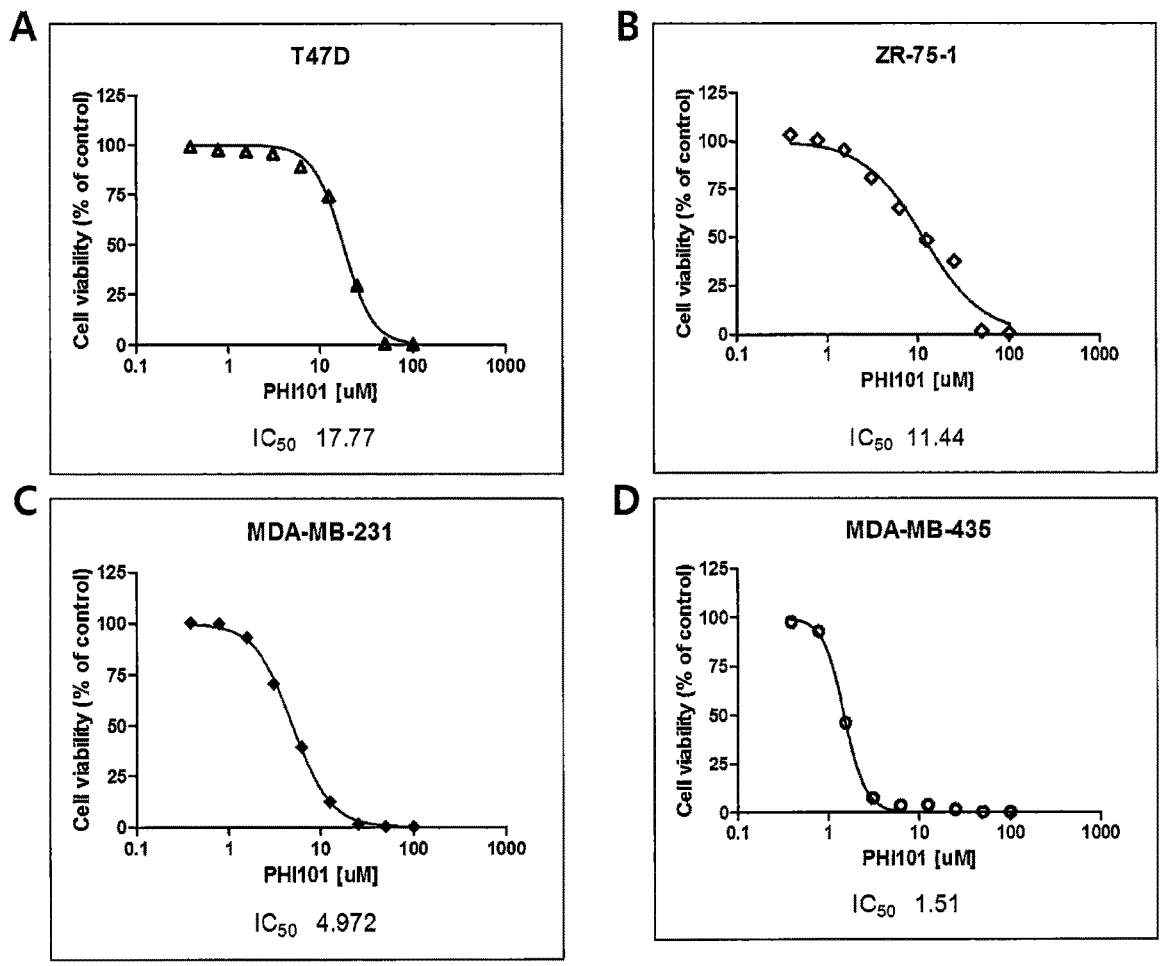
FIG. 2 depicts graphs showing the concentration-dependent effects of PHI-101 on the cell viabilities of T47D (A) and ZR-75-1 (B), which are non-triple-negative breast cancer cell lines, and MDA-MB-231 (C) and MDA-MB-435 (D), which are triple-negative breast cancer cell lines.
Figure 3:
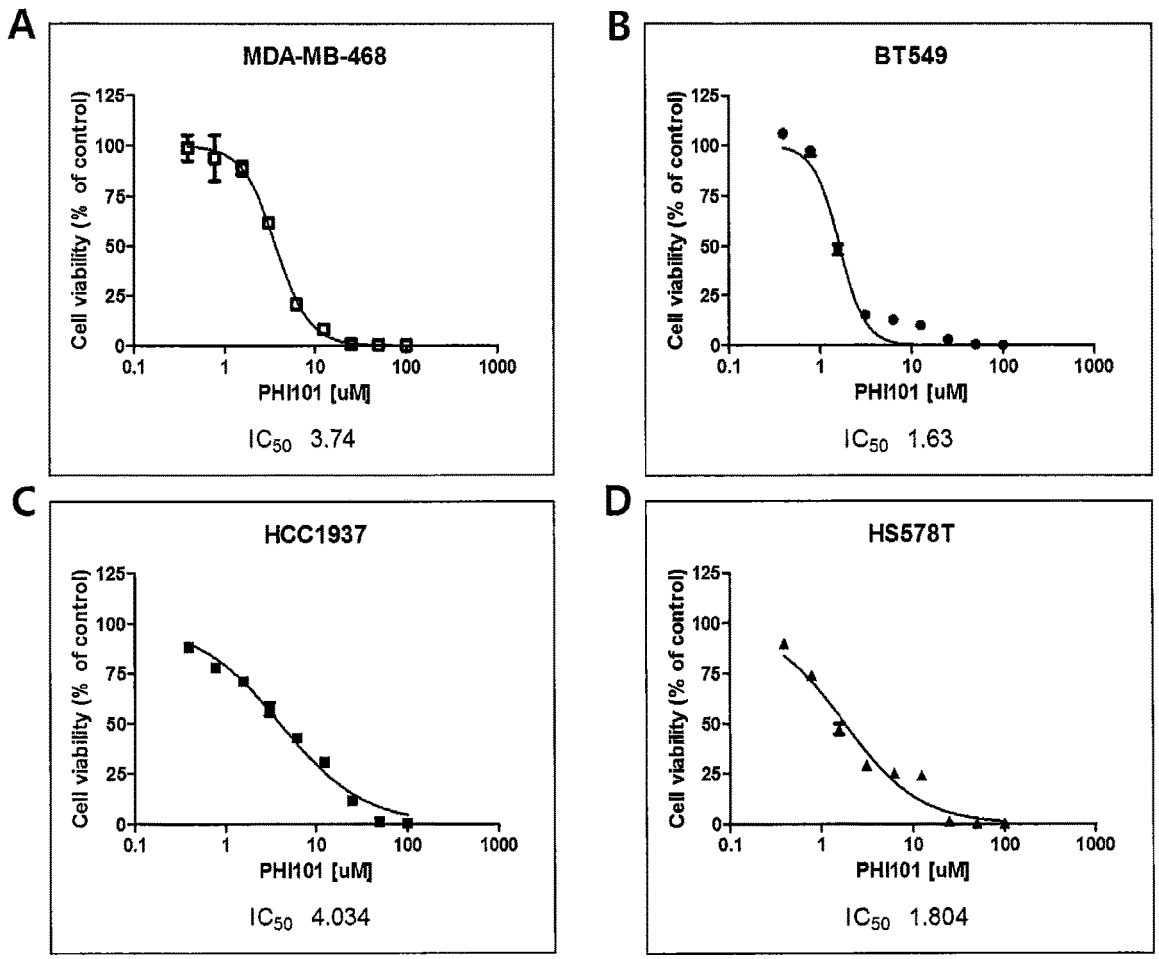
FIG. 3 depicts graphs showing the concentration-dependent effects of PHI-101 on the cell viabilities of MDA-MB-468 (A), BT549 (B), HCC1937 (C) and HS578T (D), which are tripe-negative breast cancer cell lines.

The $IC_{50}$ of PHI-101 for each breast cancer cell line was calculated by sigmoidal curve fitting using the PRIZM software, and the results of the calculation are shown in Table 2 below. It was confirmed that PHI-101 had excellent ability to inhibit the breast cancer cell lines, and that PHI-101 also had excellent ability to inhibit the triple-negative breast cancer cell lines (FIGS. 1 to 3).

TABLE 2

| Cell line | $IC_{50}$ (μM) |
|---|---|
| BT474 | 14.7 |
| JIMT1 | 0.2703 |
| MCF7 | 3.705 |
| SK-BR-3 | 4.109 |
| T47D | 17.77 |
| ZR-75-1 | 11.44 |
| MDA-MB-231 | 4.972 |
| MDA-MB-435 | 1.51 |
| MDA-MB-468 | 3.74 |
| BT549 | 1.63 |
| HCC1937 | 4.034 |
| HS578T | 1.804 |

Example 2. Evaluation of Inhibitory Activity of Combination Formulation of PHI-101 and Cisplatin Against Triple-Negative Breast Cancer Cell Lines Each of the breast cancer cell lines shown in Table 3 below was cultured using RPMI-1640 in a 100-mm culture dish, and then diluted to a density of 3,000 cells/90 μl using PBS.

TABLE 3

| Cell line | Source | Cat # | Remarks |
|---|---|---|---|
| BT474 | ATCC | HTB-20 | Non-triple-negative breast cancer |
| MCF7 | ATCC | HTB-22 | |
| T47D | ATCC | HTB-133 | |
| ZR-75-1 | ATCC | CRL-1500 | |
| BT549 | ATCC | HTB-122 | Triple-negative breast cancer |

Thereafter, 90 μl of each of the diluted breast cancer cell lines was treated with 10 μl of a 1:2 serial dilution of a hydrochloride salt of PHI-101 to a final concentration of up to 100 μM and cultured under 5% $CO_2$ at 37° C. for 1 hour, and then treated with cisplatin at an $IC_{50}$ concentration for each cell line. Groups treated with PHI-101 alone were additionally treated with 10 μl of medium instead of cisplatin. Next, each of the cell lines was cultured under 5% $CO_2$ at 37° C. for 72 hours. Next, the cells were counted using a Celltiter-Glo assay kit (Promega), and cell viability was measured by expressing the cell count as a percentage relative to that of a control group not treated with PHI-101 and cisplatin.

Figure 4:
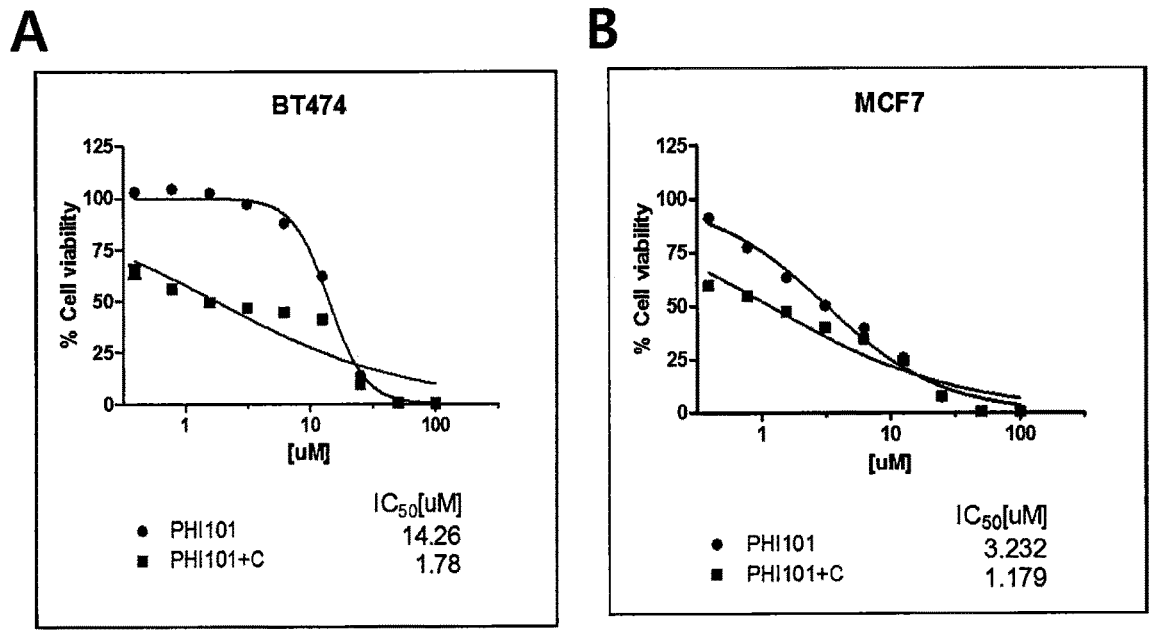
FIG. 4 depicts graphs showing the concentration-dependent effects of PHI-101 alone or a combination of PHI-101 and cisplatin (PHI-101+C) on the cell viabilities of BT474 (A) and MCF73 (B), which are non-triple-negative breast cancer cell lines.
Figure 5:
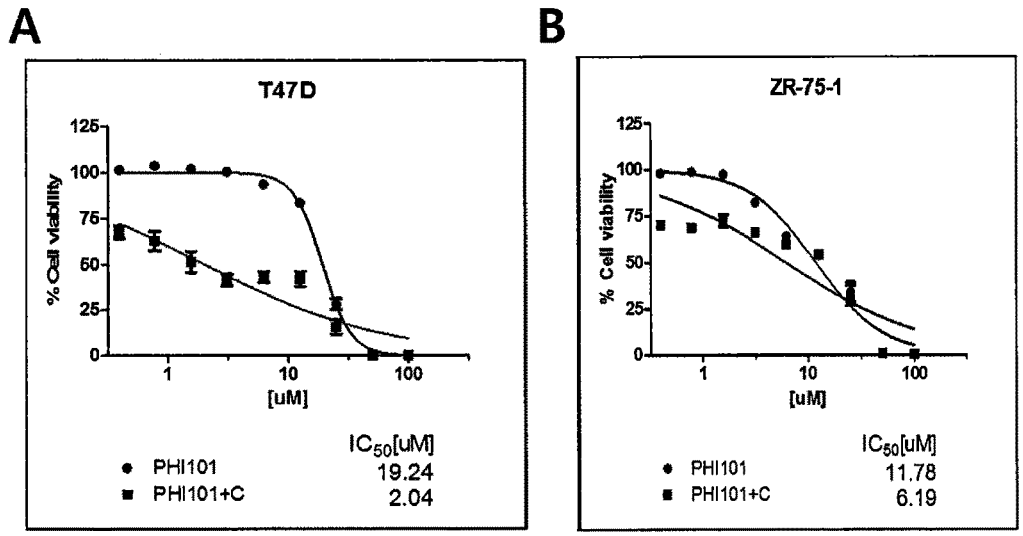
FIG. 5 depicts graphs showing the concentration-dependent effects of PHI-101 alone or a combination of PHI-101 and cisplatin on the cell viabilities of T47D (A) and ZR-75-1 (B), which are non-triple-negative breast cancer cell lines.
Figure 6:
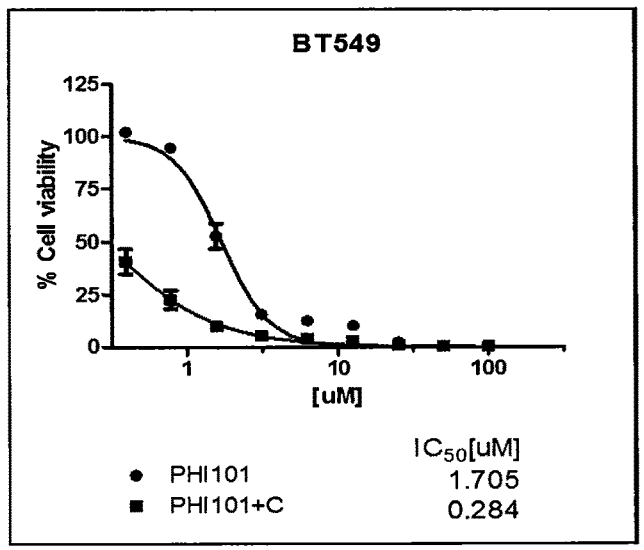
FIG. 6 is a graph showing the concentration-dependent effects of PHI-101 alone or a combination of PHI-101 and cisplatin on the cell viability of BT549 which is a triple-negative breast cancer cell line.
Figure 7:
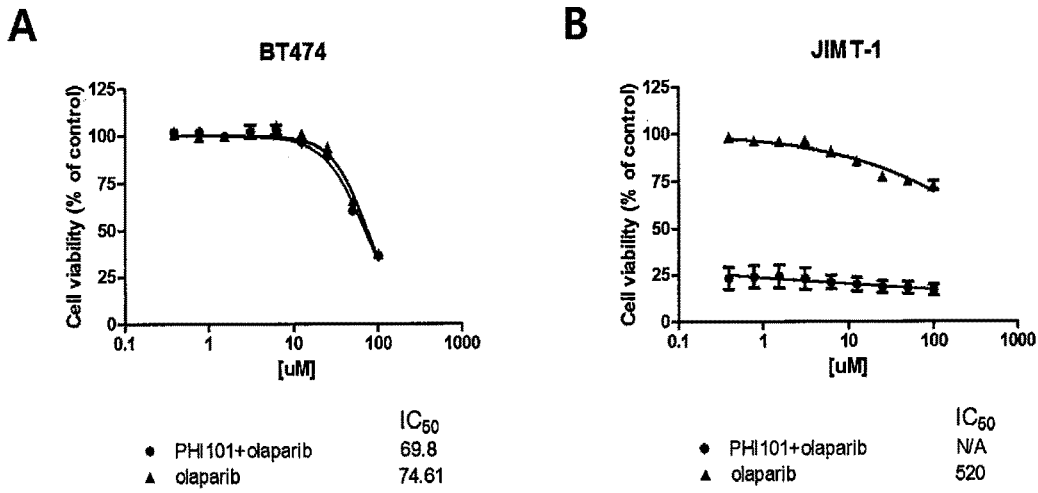
FIG. 7 depicts graphs showing the concentration-dependent effects of olaparib alone or a combination of PHI-101 and olaparib on the cell viabilities of BT474 (A) and JIMT1 (B), which are non-triple-negative breast cancer cell lines.

$IC_{50}$ for each breast cancer cell line was calculated by sigmoidal curve fitting using the PRIZM software, and the results of the calculation are shown in Table 4 below. It was confirmed that the combination of PHI-101 and cisplatin had an excellent effect against breast cancer, and that the $IC_{50}$ of the combination was particularly lower for the triple-negative breast cancer cell line BT549 than for the non-triple-negative breast cancer cell lines (FIGS. 4 to 6).

TABLE 4

| Cell line | $IC_{50}$ (μM) of PHI-101 alone | $IC_{50}$ (μM) of combination of PHI-101 + cisplatin |
|---|---|---|
| BT474 | 14.26 | 1.78 |
| MCF7 | 3.232 | 1.179 |
| T47D | 19.24 | 2.04 |
| ZR-75-1 | 11.78 | 6.19 |
| BT549 | 1.705 | 0.284 |

Example 3. Evaluation of Inhibitory Activity of Combination Formulation of PHI-101 and Olaparib Against Triple-Negative Breast Cancer Cell Lines Each of the breast cancer cell lines shown in Table 5 below was cultured with DMEM (Dulbecco's Modified Eagle Medium) or RPMI1640 in a 100-mm culture dish (SPL), and then diluted to a density of 3,000 cells/90 μl using PBS (phosphate-buffered saline) (Biosesang).

TABLE 5

| Cell line | Source | Cat # | Remarks |
|---|---|---|---|
| BT474 | ATCC | HTB-20 | Non-triple-negative breast cancer |
| JIMT1 | DSMZ | ACC589 | |
| MCF7 | ATCC | HTB-22 | |
| SK-BR-3 | ATCC | HTB-30 | |
| T47D | ATCC | HTB-133 | |
| ZR-75-1 | ATCC | CRL-1500 | |
| MDA-MB-468 | ATCC | HTB-132 | Triple-negative breast cancer |
| HS578T | ATCC | HTB-126 | |

Thereafter, 90 μl of each of the diluted breast cancer cell lines was treated with 10 μl of a 1:2 serial dilution of olaparib to a final concentration of up to 100 μM, and cultured under 5% $CO_2$ at 37° C. for 1 hour. Then, each breast cancer cell line was treated with a hydrochloride salt of PHI-101 to a final concentration of 1 μM. Groups treated with olaparib alone were additionally treated with 10μ of medium instead of PHI-101. Thereafter, each cell line was cultured under 5% $CO_2$ at 37° C. for 72 hours. Then, the cells were counted using a Celltiter-Glo assay kit (Promega), and cell viability was measured by expressing the cell count as a percentage relative to that of a control group not treated with PHI-101 and olaparib.

$IC_{50}$ for each breast cancer cell line was calculated by sigmoidal curve fitting using the PRIZM software, and the results of the calculation are shown in Table 6 below. It was confirmed that the combination of PHI-101 and olaparib had an excellent effect against the triple-negative breast cancer lines MDA-MB-468 and HS578T (FIGS. 7 to 10).

TABLE 6

| Cell line | $IC_{50}$ (μM) of olaparib alone | $IC_{50}$ (μM) of combination of olaparib + PHI-101 |
|---|---|---|
| BT474 | 74.61 | 69.8 |
| JIMT1 | 520 | — |
| MCF7 | 98.02 | 171.2 |
| SK-BR-3 | 127.4 | 71.26 |
| T47D | 77.01 | 69.65 |
| ZR-75-1 | 352.4 | 253.4 |
| MDA-MB-468 | 47.1 | 5.197 |
| HS578T | 186.2 | 9.107 |

Thereby, it was confirmed that PHI-101 may be effectively used alone or in combination with another anticancer drug (cisplatin or olaparib) to prevent or treat triple-negative breast cancer.

Example 4. Evaluation of Inhibitory Activity of Combination Formulation of PHI-101 and PARP Inhibitor Against Triple-Negative Breast Cancer Cell Lines 4-1. Evaluation of Synergistic Effect of Combination Formulation of PHI-101 and Rucaparib Against Triple-Negative Breast Cancer Cell Line The breast cancer cell line MDA-MB-468 was cultured with DMEM (Dulbecco's Modified Eagle Medium) in a 100-mm culture dish (SPL), and then diluted to a density of 2,000 cells/80 μl using PBS (phosphate-buffered saline) (Biosesang).

Thereafter, 80 μl of the diluted breast cancer cell line was treated with 10 μl of a 1:2 serial dilution of the PARP inhibitor rucaparib to a final concentration of up to 84 μM and cultured under 5% $CO_2$ at 37° C. for 1 hour. After culture, the cell line was treated with 10 μl of a 1:2 serial dilution of a hydrochloride salt of PHI-101 to a final concentration of up to 12 μM. Subsequently, the cell line was cultured under 5% $CO_2$ at 37° C. for 72 hours. Then, the cells were counted using a Celltiter-Glo assay kit (Promega), and cell viability was measured by expressing the cell count as a percentage relative to that of a control group not treated with PHI-101 and rucaparib.

$IC_{50}$ was calculated by sigmoidal curve fitting using the PRIZM software, and as a result, it was confirmed that the combination of PHI-101 and rucaparib exhibited a synergistic effect on the inhibition of the breast cancer cell line MDA-MB-468 (FIG. 11).

4-2. Evaluation of Inhibitory Activity of Combination Formulation of PHI-101 and Talazoparib or Veliparib Against Triple-Negative Breast Cancer Cell Lines The breast cancer cell line MDA-MB-468 or HS578T was cultured with DMEM (Dulbecco's Modified Eagle Medium) in a 100-mm culture dish (SPL), and then diluted to a density of 2,000 cells/90 μl using PBS (phosphate-buffered saline) (Biosesang).

Thereafter, 90 μl of each of the diluted breast cancer cell lines was treated with 10 μl of a 1:10 serial dilution of the PARP inhibitor talazoparib or veliparib to a final concentration of up to 100 μM and cultured under 5% $CO_2$ at 37° C. for 1 hour. After culture, each cell line was treated with a hydrochloride salt of PHI-101 to a concentration of 3 μM which is an $IC_{50}$ concentration. Groups treated with the PARP inhibitor alone were further treated with 10 μl of medium instead of PHI-101. Subsequently, each of the cell lines was cultured under 5% $CO_2$ at 37° C. for 72 hours. Then, the cells were counted using a Celltiter-Glo assay kit (Promega), and cell viability was measured by expressing the cell count as a percentage relative to that of a control group not treated with PHI-101 and the PARP inhibitor.

$IC_{50}$ was calculated by sigmoidal curve fitting using the PRIZM software, and as a result, it was confirmed that the combination of PHI-101 and talazoparib (FIG. 12) or veliparib (FIG. 13) exhibited an excellent effect on the inhibition of the breast cancer cell lines MDA-MB-468 and HS578T.

Thereby, it was confirmed that PHI-101 may be effectively used in combination to the PARP inhibitor to prevent or treat triple-negative breast cancer.

Example 5. Evaluation of Inhibitory Activity of Combination Formulation of PHI-101 and Olaparib Against Triple-Negative Breast Cancer in Mouse 5-1. Method for Evaluating Tumor Inhibitory Activity of Combination Formulation of PHI-101 and Olaparib 5-1-1. Cell Culture The breast cancer cell line MDA-MB-468 was monolayer-cultured in an L-15 medium supplemented with 10% heat-inactivated fetal bovine serum under 5% $CO_2$ at 37° C. The tumor cells were subcultured so as not to exceed passages 4 to 5 before confluence by trypsin-EDTA treatment. The tumor cells growing in an exponential growth phase were harvested and counted for tumor inoculation.

5-1-2. Mouse Preparation

As mice, 6-8-week-old NOD SCID female mice (18 to 22 g) (GemPharmatech Co., Ltd) were prepared. The mice were quarantined for 7 days before use in the experiment, and mice with abnormal health were excluded from the experiment. The mice were housed in cages (300×180×150 mm) at 22±3° C. and a relative humidity of 40% to 70% under a 12-hour light/12-hour dark cycle. During the entire experimental period except for the period specified by the protocol, the mice were allowed to freely access sterilized dry granular food (Beijing Keaoxieli Feed Co., Ltd., Beijing, China) and water.

5-1-3. Tumor Inoculation

For tumor induction, MDA-MB-468 breast cancer cells ($1×10^7$) in 0.1 ml of a mixture (1:1) of L-15 and Matrigel (BD, cat. No. 356234) were injected subcutaneously into the right flank of each mouse. When the average tumor volume reached 179 $mm^3$, as shown in Table 7 below, each group was treated with a hydrochloride salt of PHI-101 and/or olaparib for 28 days. Then, five mice were allocated for each group so that the average tumor volume was the same between the groups at the time point of treatment.

TABLE 7

| Group # | Active ingredient | Dose (mg/kg/day) | Dose volume (μl/g) | Regimen (times/day) |
|---|---|---|---|---|
| G1 | Vehicle control | — | 10 | 1 |
| G2 | Olaparib | 50 | 10 | 2 |
| G3 | PHI-101 | 60 | 10 | 1 |
| G4 | Olaparib | 50 | 10 | 2 |
|    | PHI-101 | 60 |    | 1 |

5-1-4. Measurement Parameters

For all the mice, tumor growth, behavior such as mobility, food and water consumption (cage side examination), body weight (BW), eye/head matting and other abnormal effects were monitored, and mortality and/or abnormal clinical symptoms were recorded.

5-1-5. Body Weight

The body weight of each mouse was measured twice a week, and the change (%) in body weight (BW) was calculated using the following equation.

BW change (%)=($BW_{PG-Dx}$/$BW_{PG-D1}$)×100

$BW_{PG-Dx}$=measured body weight
$BW_{PG-D1}$=initial body weight 5-1-6. Tumor Volume and Tumor Growth Inhibition Rate Measurement of the tumor volume was performed with calipers twice a week. The tumor volume (TV) (mm$^3$) was calculated using the following equation.

TV=$a \times b^2/2$ a=long diameter of tumor
b=short diameter of tumor

The tumor growth inhibition (TGI) rate was calculated according to the following equation using the tumor volume.

TGI (%)=(1−T/C)×100

T=final tumor volume of experimental group/initial tumor volume of experimental group
C=final tumor volume of control group/initial tumor volume of control group 5-1-7. Criteria for Termination of Experiment Mice whose condition deteriorated continuously or whose tumor volume was observed to exceed 3,000 mm$^3$ (individual tumor or population average>3,000 mm$^3$) were euthanized before death or before reaching coma. Mice showing obvious signs of severe distress and/or pain were sacrificed by carbon dioxide inhalation, and then the cervical spine was dislocated. In addition, mice with significant weight loss (weight loss of more than 20%) or mice not ingesting sufficient food or water were euthanized.

5-1-8. Statistical Analysis

Statistical analysis was performed with a significance level of 5% or P<0.05, and the mean and standard deviation of each group were calculated for all parameters. After performing a two-way RM ANOVA for the average, Tukey's post hoc comparisons were performed.

5-2. Evaluation of Tumor Inhibitory Activity of Combination Formulation of PHI-101 and Olaparib 5-2-1. Examination as to Whether Mouse Body Weight was Maintained In order to evaluate whether PHI-101 and/or olaparib affected the body weight of each mouse, the change in the body weight of each mouse was analyzed according to Example 5-1-5.

As a result, it was confirmed that no significant change in the body weight of each mouse was observed during the experiment (FIG. 14), indicating that that PHI-101 and/or olaparib did not affect the body weight of each mouse.

5-2-2. Evaluation of Tumor Inhibitory Activity of Combination Formulation of PHI-101 and Olaparib In order to evaluate whether PHI-101 and/or olaparib affects tumor inhibition in the mice, the volume and growth inhibition rate of the tumor generated by the breast cancer cell line MDA-MB-468 transplanted into the mice were analyzed according to Example 5-1-6.

As a result, it was shown that the tumor growth inhibition rate was higher in the group treated with the combination of PHI-101 and olaparib than in the group treated with PHI-101 alone or olaparib alone (Table 8 and FIG. 15).

TABLE 8

| Group # | Tumor volume (52 days) (mm$^3$) | T/C (%) | TGI (%) | P Value |
|---|---|---|---|---|
| G1 | 531 ± 6 | — | — | — |
| G2 | 402 ± 25 | 76 | 24 | P < 0.001 |
| G3 | 443 ± 18 | 84 | 16 | P < 0.05 |
| G4 | 303 ± 16 | 58 | 42 | P < 0.0001 |

Therefore, it was confirmed that effective inhibition of triple-negative breast cancer is possible by the combination of PHI-101 and olaparib.

Example 6. Evaluation of Inhibitory Activity Against Herceptin-Resistant Breast Cancer Cell Line 6-1. Method for Evaluating Tumor Inhibitory Activity 6-1-1. Cell Culture The Herceptin-resistant breast cancer cell line JIMT-1 was monolayer-cultured in an L-15 medium supplemented with 10% heat-inactivated fetal bovine serum under 5% $CO_2$ at 37° C. The tumor cells were subcultured so as not to exceed passages 4 to 5 before confluence by trypsin-EDTA treatment. The tumor cells growing in an exponential growth phase were harvested and counted for tumor inoculation.

6-1-2. Mouse Preparation

As mice, 7-8-week-old NOD SCID female mice (20 to 22 g) (GemPharmatech Co., Ltd.) were prepared. The mice were quarantined for 7 days before use in the experiment, and mice with abnormal health were excluded from the experiment. The mice were housed in cages (300×180×150 mm) at 22±3° C. and a relative humidity of 40% to 70% under a 12-hour light/12-hour dark cycle. During the entire experimental period except for the period specified by the protocol, the mice were allowed to freely access sterilized dry granular food (Beijing Keaoxieli Feed Co., Ltd., Beijing, China) and water.

6-1-3. Tumor Inoculation

For tumor induction, JIMT-1 breast cancer cells (1×10$^6$) in 0.1 ml of PBS were injected subcutaneously into the right flank of each mouse. When the average tumor volume reached 75 mm$^3$, as shown in Table 9 below, each group was treated with Herceptin or a hydrochloride salt of PHI-101 for 3 weeks. Then, five mice were allocated for each group so that the average tumor volume was the same between the groups at the time point of treatment.

TABLE 9

| Group # | Active ingredient | Dose (mg/kg/day) | Dose volume (μl/g) | Regimen (times/day) |
|---|---|---|---|---|
| G1 | Vehicle control | — | 10 | 1 |
| G2 | Herceptin | 5 | 10 | 5 |
| G3 | PHI-101 | 60 | 10 | 1 |

6-1-4. Measurement Parameters

For all the mice, tumor growth, behavior such as mobility, food and water consumption (cage side examination), body weight (BW), eye/head matting and other abnormal effects were monitored, and mortality and/or abnormal clinical symptoms were recorded.

6-1-5. Tumor Volume and Tumor Growth Inhibition Rate

Measurement of the tumor volume was performed with calipers twice a week. The tumor volume (TV) (mm³) was calculated using the following equation.

$$TV = a \times b^2 / 2$$

a=long diameter of tumor
b=short diameter of tumor

The tumor growth inhibition (TGI) rate was calculated according to the following equation using the tumor volume.

$$TGI\ (\%) = (1 - T/C) \times 100$$

T=final tumor volume of experimental group/initial tumor volume of experimental group
C=final tumor volume of control group/initial tumor volume of control group 6-1-6. Criteria for Termination of Experiment Mice whose condition deteriorated continuously or whose tumor volume was observed to exceed 3,000 mm³ (individual tumor or population average>3,000 mm³) were euthanized before death or before reaching coma. Mice showing obvious signs of severe distress and/or pain were sacrificed by carbon dioxide inhalation, and then the cervical spine was dislocated. In addition, mice with significant weight loss (weight loss of more than 20%) or mice not ingesting sufficient food or water were euthanized.

6-1-7. Statistical Analysis

Statistical analysis was performed with a significance level of 5% or P<0.05, and the mean and standard deviation of each group were calculated for all parameters. After performing a two-way RM ANOVA for the average, Tukey's post hoc comparisons were performed.

6-2. Evaluation of Inhibitory Activity of PHI-101 Against Herceptin-Resistant Tumor In order to evaluate whether PHI-101 has an effect on tumor inhibition in the mice, the volume and growth inhibition rate of the tumor generated by the breast cancer cell line JIMT-1 transplanted into the mice were analyzed by performing Example 6-1-5.

As a result, it was shown that the growth inhibition rate of the Herceptin-resistant tumor was higher in the group treated with PHI-101 at a dose of 60 mg/kg/day than in the group treated with Herceptin (FIG. 16). Therefore, it was confirmed that effective inhibition of Herceptin-resistant breast cancer is possible by treatment with PHI-101.

So far, the present disclosure has been described with reference to the embodiments. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

What is claimed is:

1. A method for treating breast cancer, the method comprising a step of administering to a subject in need thereof pharmaceutical composition containing a compound represented by the following Formula 1 or a pharmaceutically acceptable salt thereof,
   wherein the breast cancer is triple-negative breast cancer or Herceptin-resistant breast cancer:

[Formula 1]

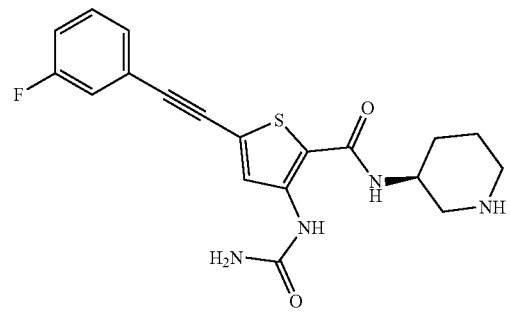

2. The method of claim 1, wherein the pharmaceutical composition further contains cisplatin.

3. The method of claim 1, wherein the pharmaceutical composition further contains a poly(ADP-ribose) polymerase (PARP) inhibitor.

4. The method of claim 3, wherein the PARP inhibitor is one or more anticancer drugs selected from the group consisting of olaparib, rucaparib, talazoparib and veliparib.

5. The method of claim 1, wherein the pharmaceutically acceptable salt is a hydrochloride salt.

* * * * *